US010292667B2

(12) United States Patent
Shah

(10) Patent No.: US 10,292,667 B2
(45) Date of Patent: *May 21, 2019

(54) IMAGE ACQUISITION OPTIMIZATION

(71) Applicant: Medtronic Navigation, Inc., Louisville, CO (US)

(72) Inventor: Jigney Shah, Ashland, MA (US)

(73) Assignee: Medtronic Navigation, Inc., Louisville, CO (US)

(*) Notice: Subject to any disclaimer, the term of this patent is extended or adjusted under 35 U.S.C. 154(b) by 1297 days.

This patent is subject to a terminal disclaimer.

(21) Appl. No.: 14/286,717

(22) Filed: May 23, 2014

(65) Prior Publication Data
US 2014/0270074 A1    Sep. 18, 2014

Related U.S. Application Data

(63) Continuation of application No. 13/014,886, filed on Jan. 27, 2011, now Pat. No. 8,737,567.

(51) Int. Cl.
*A61B 6/00* (2006.01)
*H05G 1/22* (2006.01)
*G21K 1/00* (2006.01)

(52) U.S. Cl.
CPC .......... *A61B 6/405* (2013.01); *A61B 6/42* (2013.01); *A61B 6/4405* (2013.01); *A61B 6/482* (2013.01);
(Continued)

(58) Field of Classification Search
CPC .. H05G 1/34; H05G 1/32; H05G 1/20; H05G 1/54; H05G 1/60; H05G 1/22; H05G 1/30;
(Continued)

(56) References Cited

U.S. PATENT DOCUMENTS 4,149,079 A   4/1979   Ben-Zeev et al.
4,535,245 A   8/1985   Zonneveld et al.
(Continued)

FOREIGN PATENT DOCUMENTS

CN   101234025 A   8/2008
CN   101296658 A   10/2008
(Continued)

OTHER PUBLICATIONS

Japanese Office Action dated Mar. 15, 2016 for JP Application No. 2015-095117 corresponding to PCT/US2012/022542 claiming benefit of U.S. Appl. No. 13/014,886, filed Jan. 27, 2011.
(Continued)

*Primary Examiner* — Irakli Kiknadze
(74) *Attorney, Agent, or Firm* — Harness, Dickey & Pierce, P.L.C.

(57) ABSTRACT

A system and a method for acquiring image data of a subject with an imaging system is provided. The system can include a gantry that completely annularly encompasses at least a portion of the subject, with a source positioned within and movable relative to the gantry. The source can be responsive to a signal to output at least one pulse. The system can include a detector positioned within and movable relative to the gantry to detect the pulse emitted by the source. The system can also include a detector control module that sets detector data based on the detected pulse, and an image acquisition control module that sets the signal for the source and receives the detector data. The image acquisition control module can reconstruct image data based on the detector data. The signal can include a signal for the source to output a single pulse or two pulses.

24 Claims, 8 Drawing Sheets

(52) U.S. Cl.
CPC ............... *A61B 6/50* (2013.01); *A61B 6/54* (2013.01); *A61B 6/541* (2013.01)

(58) Field of Classification Search
CPC .. H05G 1/44; H05G 1/46; H05G 1/58; H05G 1/10; H05G 1/26; H05G 1/36; H05G 1/52; A61B 6/405; A61B 6/42; A61B 6/4405; A61B 6/482; A61B 6/50; A61B 6/54; A61B 6/541; A61B 6/032; A61B 6/542; A61B 6/4441; A61B 6/488; A61B 6/503; A61B 6/545; A61B 6/544; A61B 6/56; A61B 6/586; A61B 6/027; A61B 6/035; A61B 6/0407; A61B 6/4021; A61B 6/469; A61B 6/06; A61B 6/4035; A61B 6/485; A61B 6/487; A61B 6/4291; A61B 6/505; A61B 6/00; A61B 6/03; A61B 6/4042; H04N 5/32; H04N 5/374; H04N 5/378; G01T 1/2018; G01T 1/2928; H01L 21/84; H01L 27/1214; H01L 27/14609; H01L 27/14663; G01N 2223/204; G01N 2223/419; G01N 23/04; G01N 23/083; G01N 23/087; G21K 1/043; G21K 1/025; G21K 1/04; G21K 1/10; H01J 35/14; H01J 2235/062; H01J 2235/068; H01J 35/065
USPC ...................................... 378/4, 19, 106, 101
See application file for complete search history.

(56) References Cited

U.S. PATENT DOCUMENTS

| | | | |
|---|---|---|---|
| 4,614,999 A * | 9/1986 | Onodera | H05G 1/32 363/28 |
| 4,706,268 A * | 11/1987 | Onodera | H04N 5/32 348/E5.086 |
| 5,148,022 A | 9/1992 | Kawaguchi et al. | |
| 6,097,788 A | 8/2000 | Berenstein et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,203,274 B2 | 4/2007 | Charles, Jr. et al. | |
| 7,496,175 B2 | 2/2009 | Sakaguchi et al. | |
| 7,599,730 B2 | 10/2009 | Hunter et al. | |
| 7,778,382 B2 | 8/2010 | Hoffman | |
| 8,238,631 B2 | 8/2012 | Hartmann et al. | |
| 8,325,873 B2 | 12/2012 | Helm et al. | |
| 8,737,567 B2 | 5/2014 | Shah | |
| 9,014,336 B2 * | 4/2015 | Luerkens | H05G 1/10 378/106 |
| 2003/0076920 A1 | 4/2003 | Shinno et al. | |
| 2003/0133534 A1 | 7/2003 | Bothe et al. | |
| 2010/0074397 A1 | 3/2010 | Kappler et al. | |
| 2010/0239064 A1 | 9/2010 | Zhou et al. | |
| 2010/0290690 A1 | 11/2010 | Hartmann et al. | |
| 2012/0099679 A1 | 4/2012 | Yamada et al. | |
| 2012/0194183 A1 | 8/2012 | Shah | |

FOREIGN PATENT DOCUMENTS

| | | | | |
|---|---|---|---|---|
| EP | 0052394 | A1 | 5/1982 | |
| EP | 1954028 | A2 | 8/2008 | |
| EP | 2667780 | A2 | 12/2013 | |
| EP | 2653015 | B1 * | 4/2014 | ............... H05G 1/10 |
| JP | 2002325756 | A | 11/2002 | |
| JP | 2005-536288 | A | 12/2005 | |
| JP | 2006-158690 | A | 6/2006 | |
| JP | 2007319575 | A | 12/2007 | |
| JP | 2009017984 | A | 1/2009 | |
| WO | WO-2006116365 | A2 | 11/2006 | |
| WO | WO-2009109843 | A1 | 9/2009 | |
| WO | WO-2012054338 | A1 | 4/2012 | |
| WO | WO-2012103211 | A2 | 8/2012 | |

OTHER PUBLICATIONS

Japanese Office Action dated Dec. 6, 2016 for JP Application No. 2015-095117 corresponding to PCT/US2012/022542 claiming benefit of U.S. Appl. No. 12/014,886, filed Jan. 27, 2011.
Japanese Office Action dated Jan. 6, 2015 for JP Application No. 2013-551308 corresponding to PCT/US2012/022542 claiming benefit of U.S. Appl. No. 13/014,886, filed Jan. 27, 2011.
"Medtronic O-Arm Multi-Dimensional Surgical Imaging System"; Brochure, 24pp, 2009.
International Preliminary Report on Patentability and Written Opinion dated Aug. 8, 2013 for PCT/US2012/022542 claiming benefit of U.S. Appl. No. 13/014,886, filed Jan. 27, 2011.
International Search Report and Written Opinion dated Aug. 20, 2012 for PCT/US2012/022542 claiming benefit of U.S. Appl. No. 13/014,886, filed Jan. 27, 2011.
Invitation to Pay Additional Fees for PCT/US2012/022542 dated May 25, 2012, claiming benefit of U.S. Appl. No. 13/014,886, filed Jan. 27, 2011.
Japan Office Action dated May 7, 2014 for Japan Patent Application No. 2013-551308.
Chinese Office Action dated Sep. 8, 2015 for China Patent Application No. 201280010678.7.
Japanese Office Action dated Aug. 29, 2017 in corresponding Japanese Application No. 2015-095117.
Chinese Office Action dated Jul. 30, 2018 in corresponding Chinese Application No. 201610375457.X.
Japanese Office Action dated Oct. 2, 2018 in corresponding Japanese Application No. 2017-255185.

\* cited by examiner

IMAGE ACQUISITION OPTIMIZATION

CROSS-REFERENCE TO RELATED APPLICATIONS

This application is a continuation application of U.S. patent application Ser. No. 13/014,886 filed on Jan. 27, 2011, the entire disclosure of which is incorporated by reference herein.

FIELD

The present disclosure relates to imaging a subject, and particularly to an optimal image acquisition procedure for an imaging device.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, provided is a system for acquiring image data of a subject with an imaging system. The system can include a gantry that completely annularly encompasses at least a portion of the subject. The system can also include a source positioned within and movable relative to the gantry. The source can be responsive to a signal to output at least one pulse. The system can include a detector positioned within and movable relative to the gantry and the source to detect the at least one pulse emitted by the source. The system can also include a detector control module that sets detector data based on the detected at least one pulse, and an image acquisition control module that sets the signal for the source and receives the detector data. The image acquisition control module can be operable to reconstruct image data based on the detector data. The signal can include a signal for the source to output a single pulse or a signal for the source to output two pulses.

Further provided is a method for acquiring image data of a subject with an imaging system. The method can include positioning a gantry to completely annularly encompass at least a portion of the subject, with a source and a detector positioned within and movable relative to the gantry. The method can also include receiving at least one user input that provides a request for an output for the source, and determining, based on the user input, a type of output for the source. The method can include outputting one pulse with the source or substantially simultaneously outputting two pulses with the source, and receiving the one pulse or two pulses with the detector. The method can also include reconstructing, based on the one pulse or two pulses received by the detector, an image of the subject.

Also provided is a method for acquiring image data of a subject with an imaging system. The method can include positioning a gantry to completely annularly encompass at least a portion of the subject, with a source and a detector positioned within and movable relative to the gantry. The method can include outputting a first pulse having a first pulse rate with the source, and substantially simultaneously outputting a second pulse with a second pulse rate with the source, the second pulse rate being different than the first pulse rate. The method can include receiving the first pulse and the second pulse with the detector, and reconstructing, based on first pulse and the second pulse received by the detector, an image of the subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
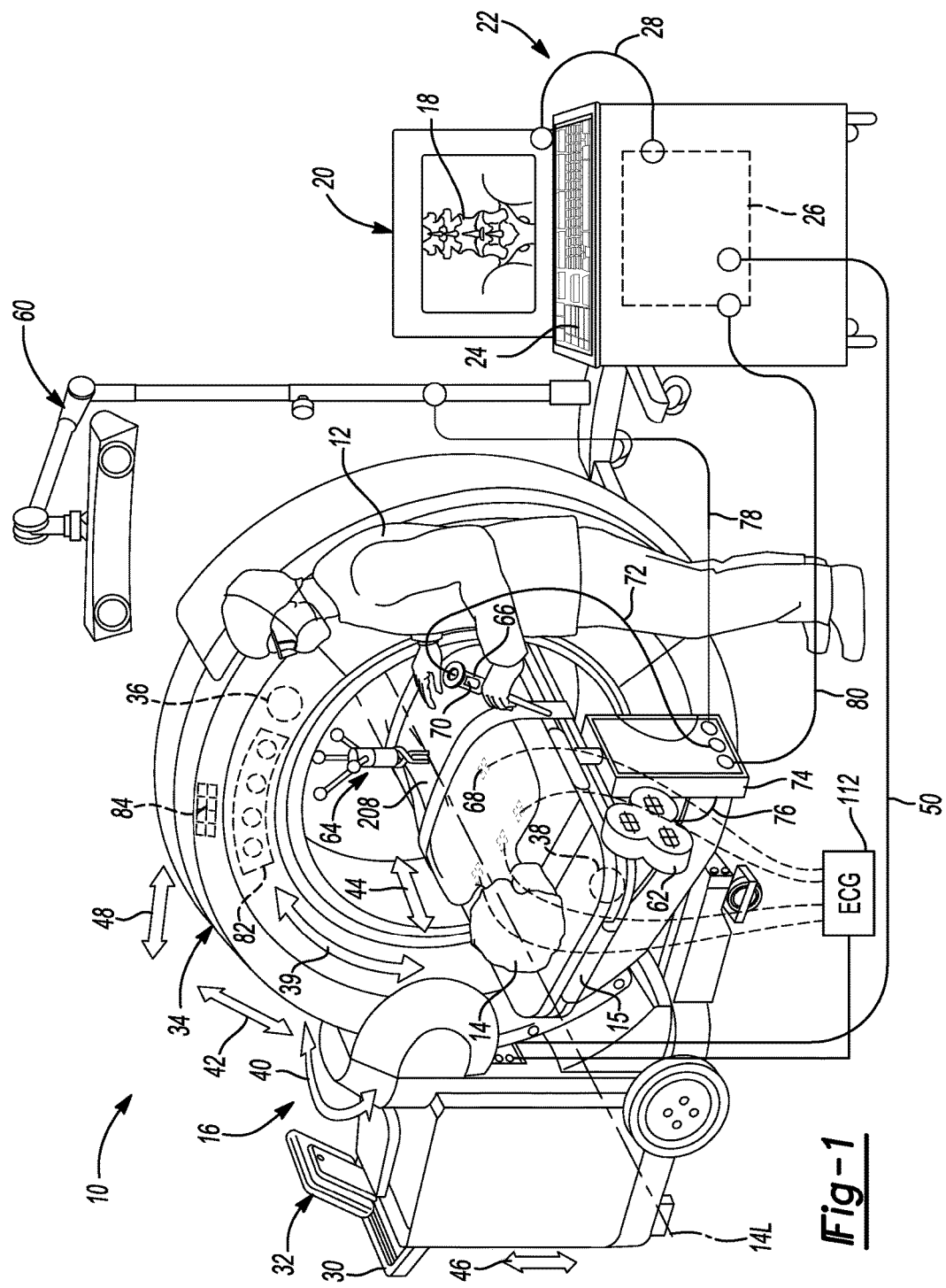
FIG. 1 is an environmental view of an exemplary imaging system in an operating theatre.

The following description is merely exemplary in nature. It should be understood that throughout the drawings, corresponding reference numerals indicate like or corresponding parts and features. As indicated above, the present teachings are directed toward providing optimized image acquisition for an imaging device, such as an O-Arm® imaging system sold by Medtronic Navigation, Inc. having a place of business in Louisville, Colo., USA. It should be noted, however, that the present teachings could be applicable to any appropriate imaging device, such as a C-arm imaging device. Further, as used herein, the term "module"

can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality. In addition, it should be noted that the values provided herein for the pulse rate in kilovolts and width in milliseconds are merely exemplary as both the pulse rate and width can vary based upon the particular patient and clinical scenario, such as in the case of a pediatric patient.

With reference to FIG. 1, in an operating theatre or operating room 10, a user, such as a user 12, can perform a procedure on a patient 14. In performing the procedure, the user 12 can use an imaging system 16 to acquire image data of the patient 14 for performing a procedure. The image data acquired of the patient 14 can include two-dimension (2D) projections acquired with an x-ray imaging system, including those disclosed herein. It will be understood, however, that 2D forward projections of a volumetric model can also be generated, also as disclosed herein.

In one example, a model can be generated using the acquired image data. The model can be a three-dimension (3D) volumetric model generated based on the acquired image data using various techniques, including algebraic iterative techniques, also as discussed further herein. Displayed image data 18 can be displayed on a display device 20, and additionally, could be displayed on a display device 32a associated with an imaging computing system 32, as will be discussed in greater detail herein. The displayed image data 18 can be a 2D image, a 3D image, or a time changing four-dimension image. The displayed image data 18 can also include the acquired image data, the generated image data, both, or a merging of both the types of image data.

It will be understood that the image data acquired of the patient 14 can be acquired as 2D projections, for example with an x-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22. The computing system 22 can include a variety of computer-readable media. The computer-readable media can be any available media that can be accessed by the computing system 22 and can include both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can comprise any suitable device to enable a user to interface with the computing system 22, such as a touchpad, touch pen, touch screen, keyboard, mouse, joystick, trackball, wireless mouse, or a combination thereof. Furthermore, while the computing system 22 is described and illustrated herein as comprising the input device 24 discrete from the display device 20, the computing system 22 could comprise a touchpad or tablet computing device, and further, that the computing system 22 could be integrated within or be part of the imaging computing system 32 associated with the imaging system 16.

A connection 28 can be provided between the computing system 22 and the display device 20 for data communication to allow driving the display device 20 to illustrate the image data 18.

The imaging system 16 can include the O-Arm® imaging system sold by Medtronic Navigation, Inc. having a place of business in Louisville, Colo., USA. The imaging system 16, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, incorporated herein by reference. Additional description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference.

Figure 2:
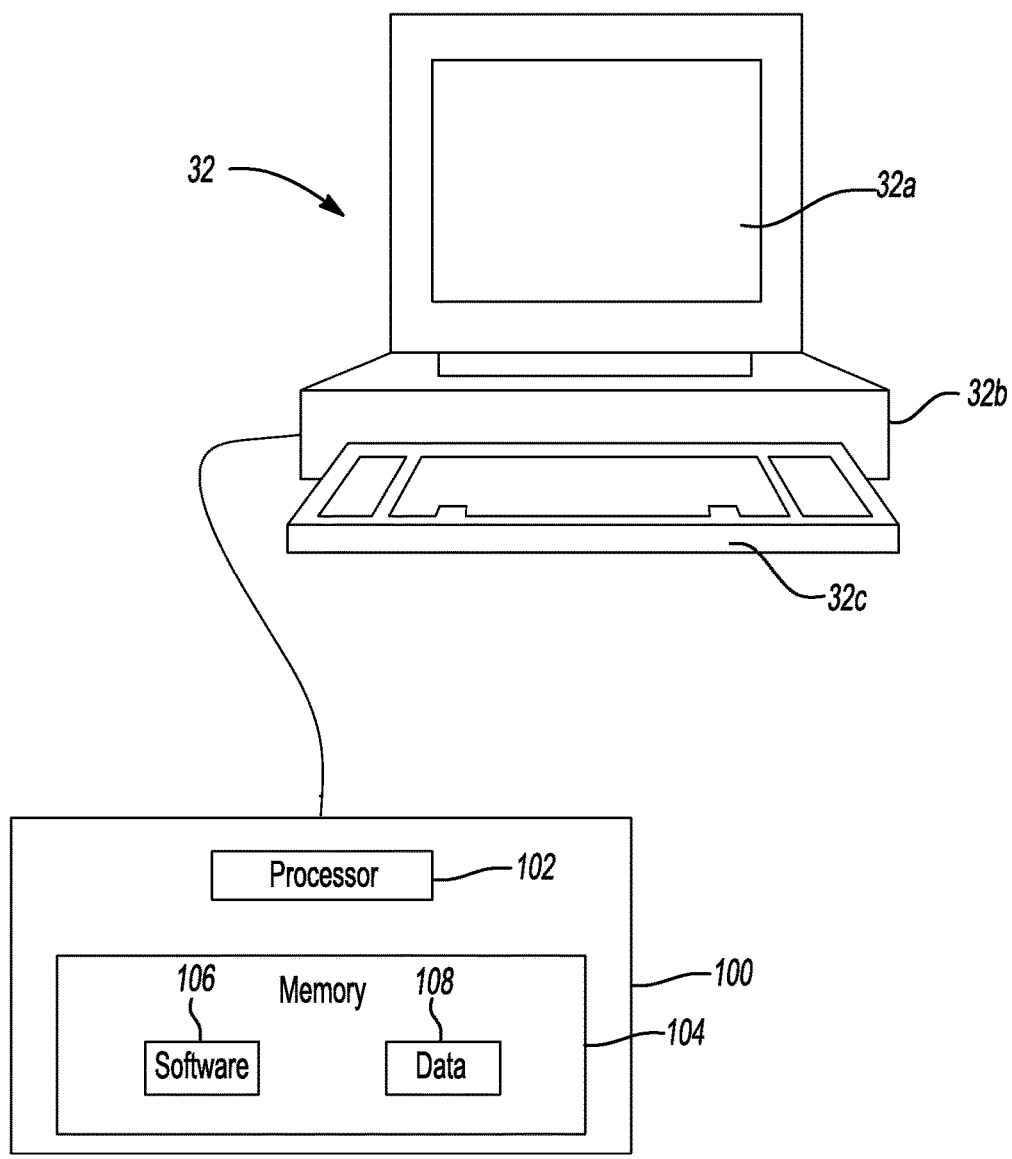
FIG. 2 is a schematic illustration of an exemplary computing system for use with the imaging system of FIG. 1.

The O-Arm® imaging system 16 can include a mobile cart 30 that includes the imaging computing system 32 and an imaging gantry 34 in which is positioned a source unit 36 and a detector 38. With reference to FIG. 2, a diagram is provided that illustrates an exemplary embodiment of the imaging computing system 32, some or all of the components of which can be used in conjunction with the teachings of the present disclosure. The imaging computing system 32 can include a variety of computer-readable media. The computer-readable media can be any available media that can be accessed by the imaging computing system 32 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

In one example, the imaging computing system 32 comprises a display device 32a and a system unit 32b. As illustrated, the display device 32a can comprise a computer video screen or monitor. The imaging computing system 32 can also include at least one input device 32c. The system unit 32b includes, as shown in an exploded view at 100, a processor 102 and a memory 104, which can include software 106 and data 108.

In this example, the at least one input device 32c comprises a keyboard. It should be understood, however, that the at least one user input device 32c can comprise any suitable device to enable a user to interface with the imaging computing system 32, such as a touchpad, touch pen, touch screen, keyboard, mouse, joystick, trackball, wireless mouse, or a combination thereof. Furthermore, while the imaging computing system 32 is described and illustrated herein as comprising the system unit 32b with the display device 32a, the imaging computing system 32 could comprise a touchpad or tablet computing device.

As will be discussed with regard to FIGS. 3-9, the imaging computing system 32 can control the source 36 and the detector 38 to optimize image data acquisition via an image acquisition control module 110, which can be stored in the memory 104 and accessed by the processor 102. A connection can be provided between the processor 102 and the display device 32a for data communication to allow driving the display device 32a to illustrate the image data 18.

With reference to FIG. 1, the mobile cart 30 can be moved from one operating theater or room to another and the gantry 34 can move relative to the mobile cart 30, as discussed further herein. This allows the imaging system 16 to be mobile allowing it to be used in multiple locations and with multiple procedures without requiring a capital expenditure or space dedicated to a fixed imaging system.

The source unit 36 can emit x-rays through the patient 14 to be detected by the detector 38. As is understood by one skilled in the art, the x-rays emitted by the source 36 can be emitted in a cone and detected by the detector 38. The source 36/detector 38 is generally diametrically opposed within the gantry 34. The detector 38 can move rotationally in a 360° motion around the patient 14 generally in the directions of arrow 39 within the gantry 34 with the source 36 remaining generally 180° from and opposed to the detector 38. Also, the gantry 34 can isometrically sway or swing (herein also referred to as iso-sway) generally in the direction of arrow 40, relative to the patient 14, which can be placed on a patient support or table 15. The gantry 34 can also tilt relative to the patient 14 illustrated by arrows 42, move longitudinally along the line 44 relative to the patient 14 and the mobile cart 30, can move up and down generally along the line 46 relative to the mobile cart 30 and transversely to the patient 14, and move perpendicularly generally in the direction of arrow 48 relative to the patient 14 to allow for positioning of the source 36/detector 38 at any desired position relative to the patient 14.

The O-Arm® imaging system 16 can be precisely controlled by the imaging computing system 32 to move the source 36/detector 38 relative to the patient 14 to generate precise image data of the patient 14. In addition, the imaging system 16 can be connected with the processor 26 via connection 50 which can include a wired or wireless connection or physical media transfer from the imaging system 16 to the processor 26. Thus, image data collected with the imaging system 16 can also be transferred from the imaging computing system 32 to the computing system 22 for navigation, display, reconstruction, etc.

Briefly, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74 as can the electromagnetic localizer 62 and/or the optical localizer 60. Using the communication lines 74, 78 respectively, the probe interface 74 can then communicate with the processor 26 with a communication line 80. It will be understood that any of the connections or communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14.

Further, the imaging system 16 can include a tracking device, such as an optical tracking device 82 or an electromagnetic tracking device 84 to be tracked with a respective optical localizer 60 or the electromagnetic localizer 62. The tracking device can be associated directly with the source 36, the detector 38, the gantry 34, or other appropriate part of the imaging system 16 to determine the location or position of the detector 38 relative to a selected reference frame. As illustrated, the tracking device 82, 84 can be positioned on the exterior of the housing of the gantry 34. Accordingly, the imaging system 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206.

Further, with continued reference to FIG. 1, the operating theatre 10 can optionally include a gating device or an electrocardiogram or ECG 112, which is attached to the patient 14, via skin electrodes, and in communication with the imaging computing system 32. Respiration and cardiac motion can cause movement of cardiac structures relative to the imaging system 16. Therefore, images can be acquired from the imaging system 16 based on a time-gated basis triggered by a physiological signal. For example, the ECG or EGM signal may be acquired from the skin electrodes or from a sensing electrode included on the instrument 66 or from a separate reference probe (not shown). A characteristic of this signal, such as an R-wave peak or P-wave peak associated with ventricular or atrial depolarization, respectively, may be used as a triggering event for the imaging computing system 32 to drive the source 36. By time-gating the acquisition of the image data 18, the image data 18 can be reconstructed to provide a 3D view of an organ of interest in a particular phase, as will be discussed in greater detail herein.

It should be noted that in a navigated procedure, the ECG 112 can also be use to time-gate the navigation data. In this regard, the characteristic of the signal, such as the R-wave peak or P-wave peak associated with ventricular or atrial depolarization, respectively, can be used as a triggering event for driving the coils in the electromagnetic localizer 62. Further detail regarding the time-gating of the navigation data can be found in U.S. Pat. No. 7,599,730, entitled "Navigation System for Cardiac Therapies," filed Nov. 19, 2002, which is hereby incorporated by reference.

Figure 3:
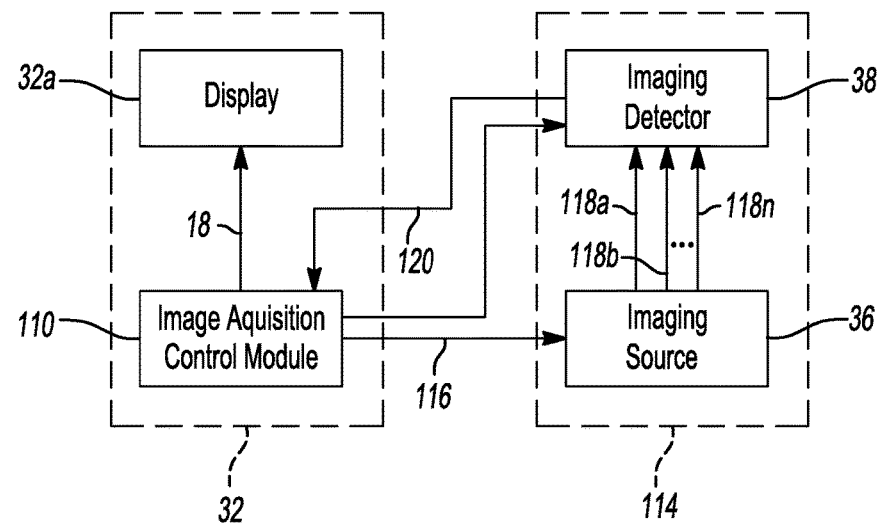
FIG. 3 is a simplified block diagram illustrating a system for implementing an image acquisition control module according to various embodiments.

With reference to FIG. 3, a simplified block diagram schematically illustrates an exemplary system 114 for implementing the image acquisition control module 110 according to various embodiments. In one example, the image acquisition control module 110 can be implemented by the imaging computing system 32 of the imaging system 16. The image acquisition control module 110 can receive user input from the input device 32c. Note that while the display is illustrated and described herein as comprising the display device 32a, the imaging computing system 32 could output image data 18 to the display device 20.

The image acquisition control module 110 can send a source output signal 116 to the source 36. As will be discussed, the source output signal 116 can comprise a signal for the source 36 to output or emit at least one or more x-ray pulses 118a . . . 118n at a particular pulse rate and pulse width.

The image acquisition control module 110 can also output a move signal 120 to the source 36 to move the position of the source 36 within the gantry 34, and the image acquisition control module 110 can also output a move signal 122 to the detector 38 to move the position of the detector 38 within the gantry 34. Generally, the source 36 and the detector 38 can move about 360° around a longitudinal axis 14L of the patient 14 within the gantry 34. The movement of the detector 38 and the source 36 relative to the patient 14 can allow the imaging system 16 to acquire image data at a plurality of selected locations and orientations relative to the subject 14.

In this regard, the 2D projection image data can be acquired by substantially annular or 360° orientation movement of the source 36/detector 38 around the patient 14 due to positioning of the source 36/detector 38 moving around the patient 14 in the optimal movement. Also, due to movements of the gantry 34, the source 36/detector 38 need never move in a pure circle, but rather can move in a spiral helix, or other rotary movement about or relative to the patient 14. Also, the path can be substantially non-symmetrical and/or non-linear based on movements of the imaging system 16, including the gantry 34 and the source 36/detector 38 together. In other words, the path need not be continuous in that the source 36/detector 38 and the gantry 34 can stop, move back from the direction from which it just came (e.g., oscillate), etc. in following the optimal path. Thus, the source 36/detector 38 need never travel a full 360° around the patient 14 as the gantry 34 may tilt or otherwise move and the source 36/detector 38 may stop and move back in the direction it has already passed. Further detail regarding the movement of the source 36 and the detector 38 can be found in U.S. Pat. No. 7,108,421, entitled "Systems and Methods for Imaging Large Field-of-View Objects," filed on Mar. 18, 2003 and incorporated herein by reference.

With continued reference to FIG. 3, the pulses 118a . . . 118n can be received by the detector 38. The detector 38 can transmit a signal 120 regarding the received pulses to the image acquisition control module 110. Based on the signal(s) 120 received from the detector 38, the image acquisition control module 110 can generate the image data 18 on the display device 32a or the display device 20.

In this regard, the image acquisition control module 110 can perform automatic reconstruction of an initial three dimensional model of the area of interest of the patient 14. Reconstruction of the three dimensional model can be performed in any appropriate manner, such as using an algebraic techniques for optimization. Appropriate algebraic techniques include Expectation maximization (EM), Ordered Subsets EM (OS-EM), Simultaneous Algebraic Reconstruction Technique (SART) and total variation minimization, as generally understood by those skilled in the art. The application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging system 16. The image acquisition control module 110 can output image data 18 to the display device 32a or the display device 20.

Figure 4:
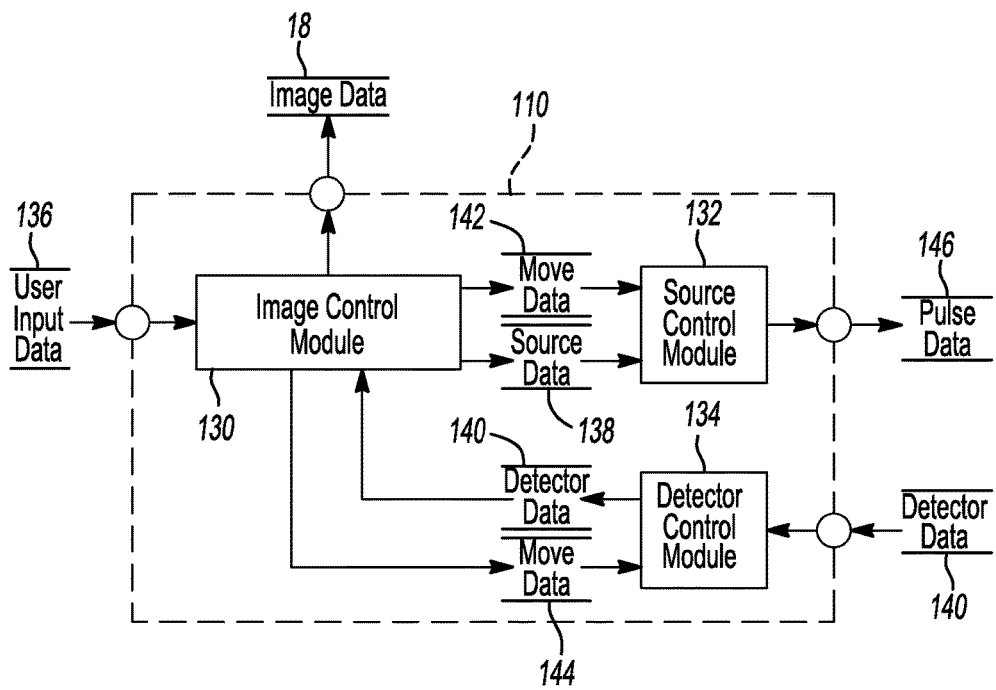
FIG. 4 is a dataflow diagram illustrating an exemplary control system performed by the image acquisition control module of FIG. 3.

With reference to FIG. 4, a dataflow diagram illustrates various components of an image acquisition control system that can be embedded within the image acquisition control module 110. The image acquisition control module 110 can control the imaging system 16 to generate the image data 18 for display on the display device 32a and/or display device 20. Various embodiments of the image acquisition control system according to the present disclosure can include any number of sub-modules embedded within the image acquisition control module 110. The sub-modules shown may be combined and/or further partitioned to similarly generate the image data 18. Further, the image acquisition control module 110 can comprise one or more software modules embodied in non-transitory, machine readable code that runs on the processor 108. Inputs to the system can be received from the input device 32c, input device 24, or even received from other control modules (not shown) within the computing system 22 or imaging computing system 32, and/or determined by other sub-modules (not shown) within the image acquisition control module 110 (not shown).

With continuing reference to FIG. 4, the image acquisition control module 110 can include an image control module 130, a source control module 132 and a detector control module 134. The image control module 130 can receive as input user input data 136. The user input data 136 can comprise input received from the input device 32c or input device 22. The user input data 136 can comprise a request for the imaging system 16 to perform a particular form of imaging. For example, the user input data 136 could comprise a request for the imaging system 16 to perform gated imaging. In another example, the user input data 136 could comprise a request for the imaging system 16 to perform dual energy imaging, or single energy imaging. Based on the user input data 136, the image control module 130 can set source data 138 for the source control module 132. The source data 138 can comprise a signal to start the imaging system 16, a signal to power-down the imaging system 16, a signal to perform gated imaging, a signal to perform dual energy imaging or a signal to perform single energy imaging.

The image control module 130 can also receive as input detector data 140. The detector data 140 can comprise the energy from the pulses 118a-118n received by the detector 38. Based on the detector data 140, the image control module 130 can set move data 142 for the source control module 132 and the move data 144 for the detector control module 134. The move data 142 can comprise a signal for the source 36 to be moved to a predetermined angular position within the gantry 34 to acquire additional image data for the patient 14. The move data 144 can comprise a signal for the detector 38 to be moved to a predetermined angular position within the gantry 34 relative to the source 36 to acquire additional image data for the patient 14. The image control module 130 can also output the image data 18 based on the detector data 140. The image data 18 can comprise the reconstructed 3D image of the patient.

With continued reference to FIG. 4, the source control module 132 can receive as input the source data 138 and the move data 142 from the image control module 130. Based on the move data 142, the source 36 can move within the gantry 34 to a desired location. Based on the source data 138, the source 36 can output pulse data 146. The pulse data 146 can comprise at least one x-ray pulse, and in some instances can comprise more than one x-ray pulse, as will be discussed in greater detail herein.

The detector control module 134 can receive as input the move data 144 and the detector data 140. Based on the move data 144, the detector 38 can move within the gantry 34 to a desired location relative to the location of the source 36. The detector control module 134 can set the detector data 140 for the image control module 130.

Figure 5:
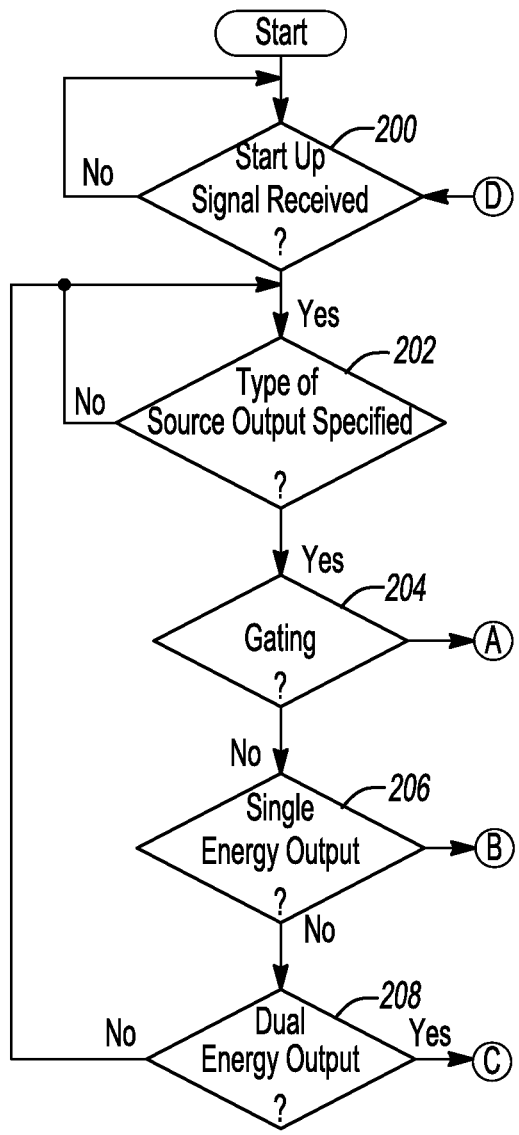
FIG. 5 is a flowchart illustrating a method performed by the image acquisition control module.

With reference now to FIG. 5, a flowchart diagram illustrates an exemplary method performed by the image acquisition control module 110. It should be noted that the flowchart diagram described herein with regard to FIGS. 5-8 is merely exemplary, as the image acquisition control module 110 could generate the image data 18 in any desired or user requested sequence. With continued reference to FIG. 5, at decision block 200, the method determines if a startup request signal has been received via the input device 32c. If not, the method loops. Otherwise, the method goes to decision block 202.

At decision block 202, the method determines if a type of energy output for the source 36 of the imaging system 16 has been specified. If a type of output for the source 36 has been specified, then the method goes to decision block 204. Otherwise, the method loops. At decision block 204, the method determines if the type of output for the source 36 is gated image acquisition. If the type of output for the source 36 is gated image acquisition, the method goes to A on FIG. 6. Otherwise, the method goes to decision block 206.

At decision block 206, the method determines if the type of output for the source 36 is a single energy output. If the output for the source 36 is single energy imaging output, then the method goes to B on FIG. 7. Otherwise, the method goes to decision block 208. At decision block 208, the method determines if the output for the source 36 is dual energy output. If the output for the source 36 is dual energy output, then the method goes to C on FIG. 8. Otherwise, the method loops to decision block 202.

Figure 6:
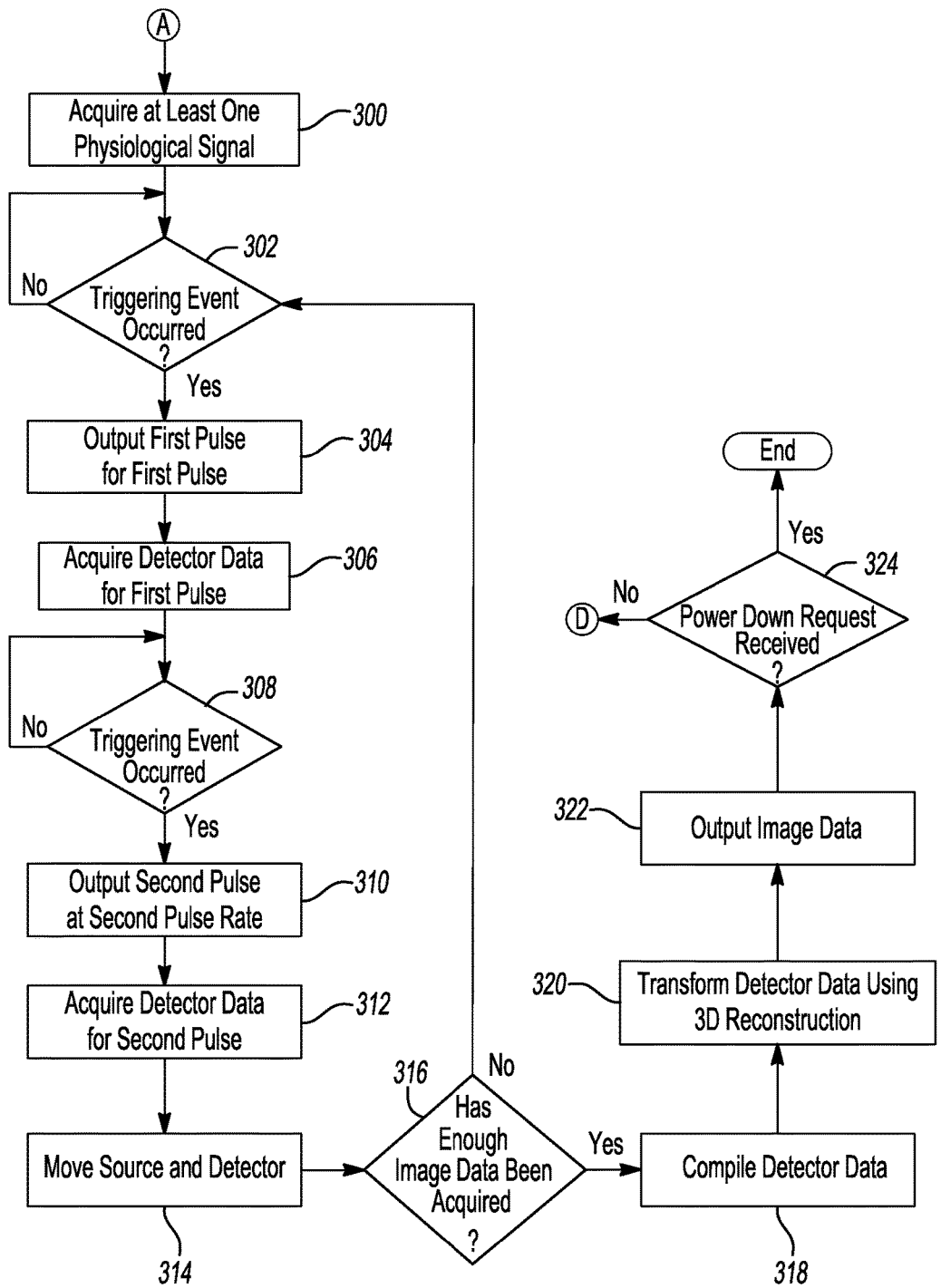
FIG. 6 is a continuation of the flowchart of FIG. 5 at A.

With reference to FIG. 6, at block 300, the method acquires at least one physiological signal. Then, at decision block 302, the method determines if a triggering event has occurred. If a triggering event has occurred, then the method goes to block 304. Otherwise, the method loops until a triggering event has occurred. At block 304, the method outputs a first pulse 118a at a first pulse rate. Then, at block 306, the method acquires detector data 140 for the first pulse 118a. At decision block 308, the method determines if another triggering event has occurred. If another triggering event has occurred, then the method goes to block 310. Otherwise, the method loops.

At block 310, the method outputs a second pulse 118b at a second pulse rate, which can have a different pulse width and height. The second pulse rate width and/or height can be greater than, less than or equal to the width and/or height of the first pulse rate. For example, the second pulse rate can have a second kilovolt (kV) value and a second width value in milliseconds (ms) and the first pulse rate can have a first kilovolt (kV) value and a first width value in milliseconds (ms), which may or may not be equal. In one example, the first kilovolt (kV) value can be from about 100 kV to about 120 kV, such as about 110 kV, and the second kilovolt (kV) value can be from about 70 kV to about 90 kV. The first width value can be from about 5 ms to about 15 ms, for example, about 10 ms, and the second current value can be from about 10 ms to about 20 ms, for example about 15 ms.

At block 312, the method acquires the detector data 140 for the second pulse 118b. At block 314, the method moves the source 36 and the detector 38. Then, at decision block 316, the method determines if enough image data has been acquired for the patient 14. In this regard, the method can determine if the source 36/detector 38 have gathered a suitable number of frames of image data to enable successful 3D reconstruction of the area of interest. In one example, the source 36/detector 38 can acquire about 180 to about 240 frames of images, which can be substantially equivalent to gathering about 360° worth of image data, even if the source 36/detector 38 does not fully circumscribe or travel 360° around the patient 14. Based on gathered image data, the image acquisition control module 110 can perform automatic reconstruction of the area of interest. Further information regarding image acquisition techniques can be found in U.S. patent application Ser. No. 12/908,186, filed on Oct. 20, 2010, entitled "Selected Image Acquisition Technique to Optimize Patient Model Construction," and incorporated by reference herein.

If enough image data has been acquired for reconstruction, then the method goes to block 318. Otherwise, the method loops to decision block 302. At block 318, the method compiles the detector data 140. At block 320, the method reconstructs the detector data 140 into the image data 18 using 3D reconstruction. At block 322, the method outputs the image data 18 to the display device 32a. At decision block 324, the method determines if a power down request has been received via the input device 32c. If a power down request has been received, the method ends. Otherwise, the method goes to D on FIG. 5.

Figure 7:
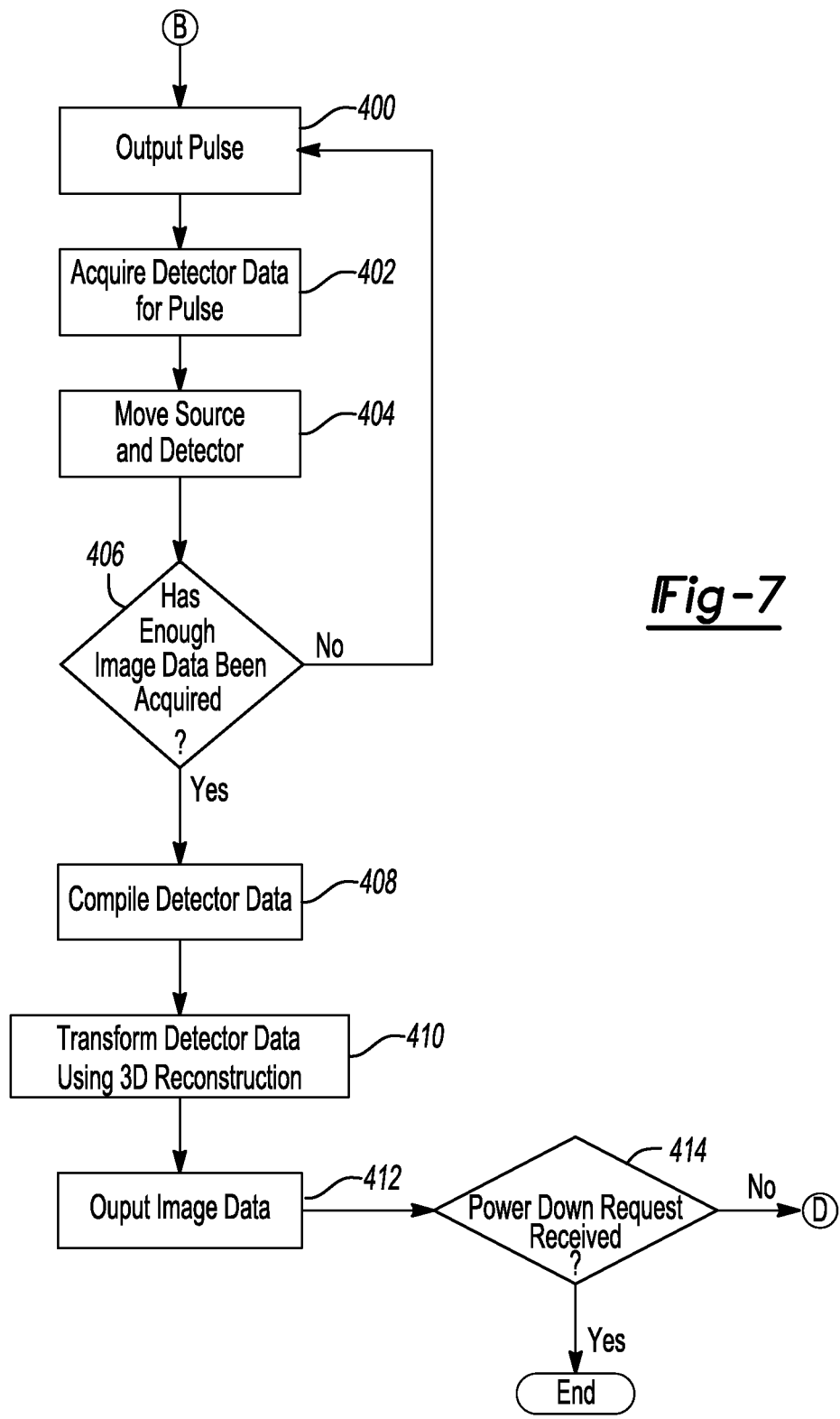
FIG. 7 is a continuation of the flowchart of FIG. 5 at B.

With reference to FIG. 7, at block 400, the method outputs a pulse 118. The pulse 118 can comprise a single pulse of energy, which can have a kilovolt (kV) value, which can be from about 80 kV to about 125 kV, The pulse width for this pulse 118 can range from about 5 ms to about 15 ms. Thus, the pulse 118 can have a wider pulse of smaller magnitude of current, which can be used in place of a larger magnitude of current pulse.

At block 402, the method acquires the detector data 140 for that pulse 118. At block 404, the method moves the source 36 and the detector 38. At decision block 406, the method determines if enough image data has been acquired for the patient 14. If enough image data has been acquired for the patient 14, then the method goes to block 408. Otherwise, the method loops to block 400. At block 408, the method compiles the detector data 140. At block 410, the method reconstructs the detector data 140 into the image data 18 using 3D reconstruction. At block 412, the method outputs the image data 18 to the display device 32a. At decision block 414, the method determines if a power down request has been received via the input device 32c. If a power down request has been received, then the method ends. Otherwise, the method goes to D on FIG. 5.

Figure 8:
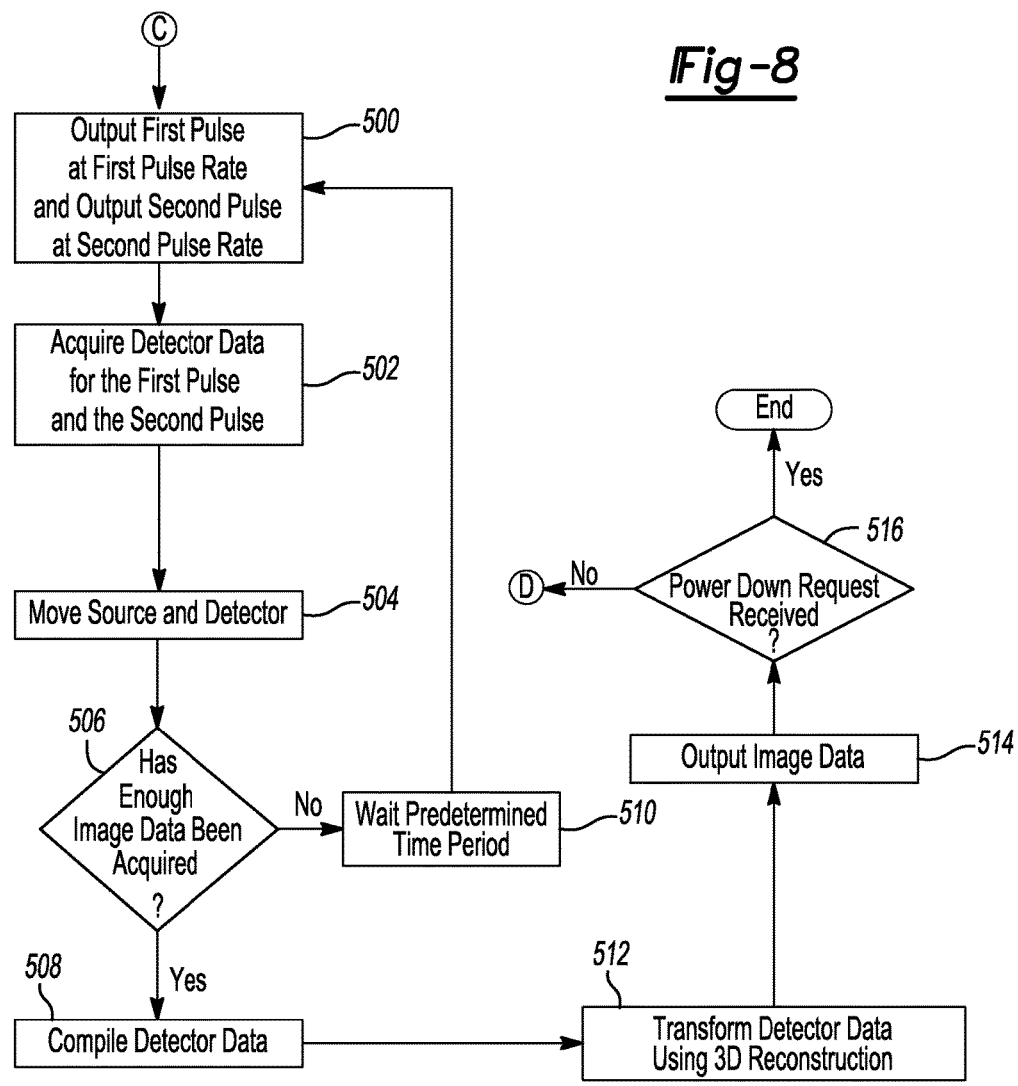
FIG. 8 is a continuation of the flowchart of FIG. 5 at C.
Figure 9:
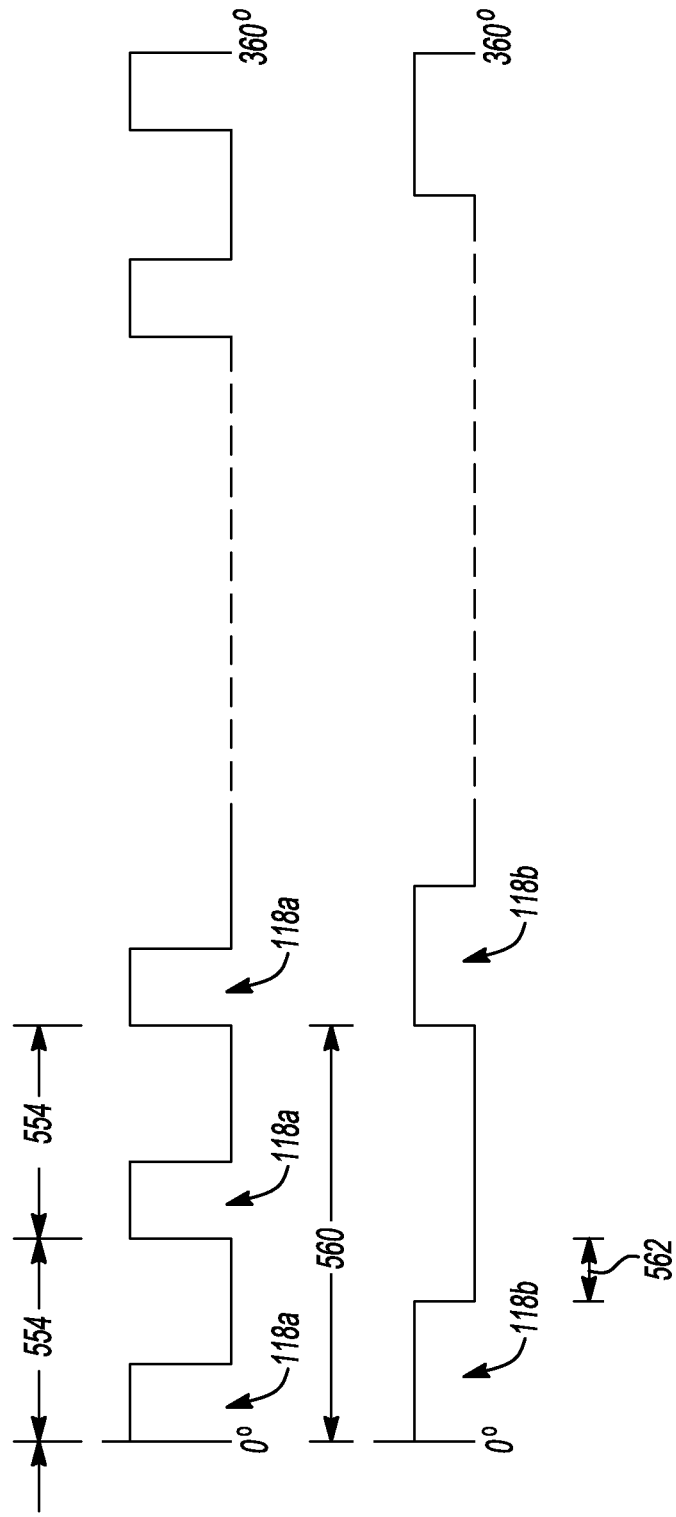
FIG. 9 is a schematic timing diagram for a dual energy output for the imaging system of FIG. 1.

With reference to FIGS. 8 and 9, at block 500, the method outputs a first pulse 118a at a first pulse rate having a first width and height and outputs a second pulse 118b at a second pulse rate having a second width and height. The second pulse rate width and/or height can be greater than, less than or equal to the first pulse rate width and/or height. For example, with reference to FIG. 9, the first pulse 118a can have a first kilovolt (kV) value 550 and a first width value 554 in milliseconds (ms). The second pulse 118b can have a second kilovolt (kV) value 556 and a second width value 560 in milliseconds (ms).

In one example, the first kilovolt (kV) value 550 can be from about 90 kV to about 120 kV such as 110 kV, and the second kilovolt (kV) value 556 can be from about 70 kV to about 90 kV, such as 80 kV. The first pulse width 554 can range from about 5 ms to about 15 ms, for example 10 ms, while the second pulse width 560 can range from about 10 ms to about 20 ms, for example 15 ms.

With reference back to FIG. 8, at block 502, the method can acquire detector data 140 for the first pulse 118a and the second pulse 118b. At block 504, the method can move the source 36 and the detector 38 by a predetermined amount. At decision block 506, the method can determine if enough image data has been acquired for the patient 14. In this regard, the method can determine if the source 36/detector 38 have gathered a suitable number of frames of image data to enable successful 3D reconstruction of the area of interest, as discussed with regard to FIG. 6.

If enough image data has been acquired for the patient 14, then the method goes to block 508. Otherwise, the method goes to block 510. At block 510, the method waits a predetermined time period for the afterglow effects to subside before the method loops to block 500.

In this regard, each pulse 118 emitted by the source 36 causes the detector 38 to glow for a period of time after the pulse 118 has been emitted ("afterglow"). In cases where the first pulse 118a and the second pulse 118b have the same pulse rate (i.e. same kilovolts and same milliamps for the same period of time), the afterglow associated with each pulse 118a, 118b will be approximately the same except for the first pulse 118a. As the afterglow is the same for each image, the effect of the afterglow can be removed from the image data 18 during processing thereby resulting in substantially undistorted image data 18. In cases where the first pulse 118a and the second pulse 118b have different pulse rates, however, the afterglow associated with each pulse can vary, and thus, the effects of the afterglow cannot be easily removed from the image data 18. Accordingly, by waiting a predetermined period of time before emitting another first pulse 118a and second pulse 118b, the detector 38 can stop glowing, thereby substantially reducing the effects of the afterglow all together. With brief reference to FIG. 9, the predetermined time period between the emission of another first pulse 118a and second pulse 118b is illustrated with reference numeral 562.

With reference back to FIG. 8, at block 508, the method can compile the detector data 140. At block 512, the method can reconstruct the detector data 140 into the image data 18 using 3D reconstruction. At block 514, the method can output the image data 18 to the display device 32a. At decision block 516, the method can determine if a power down request has been received via the input device 32c. If a power down request has been received, then the method ends. Otherwise, the method goes to D on FIG. 5.

Thus, the image acquisition control module 110 can be used to optimize the acquisition of the image data 18 by the imaging system 16. In addition, by enabling the user to select between gated image acquisition, single energy output and dual energy output from the source 36, the image acquisition can be tailored to a particular patient 14. With particular regard to gated image acquisition, the ability to gate the image acquisition to a particular physiological event can enable the user to view a selected organ of interest at a particular phase. The use of single energy output of a low current for a wider pulse width can enable a low-power generator, such as those associated with a mobile cart 30, to acquire the image data 18 at the same quality and resolution as a high-power stationary generator. The use of dual energy output can optimize the acquisition of the image data 18 by providing high resolution imaging, without increasing the radiation dose received by the patient 14. In addition, the image acquisition control module 110 can control the source 36 to emit dual energy pulses 118 without requiring a separate source 36, detector 38 and gantry 34.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A system comprising:
    a source configured to emit x-rays; and
    an image acquisition control module configured to (i) determine whether to emit a single pulse of x-rays from the source or a plurality of pulses of x-rays from the source, and (ii) generate a control signal based on the determination,
    wherein the source is configured to, in response to the control signal, emit the single pulse of x-rays or the plurality of pulses of x-rays, and
    wherein the single pulse of x-rays has a different magnitude or a different pulse width than one of the plurality of pulses of x-rays.

2. The system of claim 1, wherein:
the plurality of pulses of x-rays comprise a first pulse of x-rays and a second pulse of x-rays;
the first pulse of x-rays has a first pulse rate;
the second pulse of x-rays has a second pulse rate; and
the second pulse rate is different than the first pulse rate.

3. The system of claim 1, wherein:
the plurality of pulses of x-rays comprise a first pulse of x-rays and a second pulse of x-rays;
the source is configured to (i) output the first pulse of x-rays having a first voltage magnitude for a first period of time, and (ii) output the second pulse of x-rays having a second voltage magnitude for a second period of time;
the first voltage magnitude is different than the second voltage magnitude; and
a length of the first period of time is different than a length of the second period of time.

4. The system of claim 1, wherein the image acquisition control module is configured to (i) receive a user input signal, and (ii) generate the control signal based on the user input signal.

5. The system of claim 1, wherein:
the image acquisition control module is configured to determine whether the source is to provide (i) a gated output, (ii) emit the single pulse of x-rays, or (iii) emit the plurality of pulses of x-rays; and
the source is configured to,
in response to the signal indicating for the source to provide the gated output, emit from the source a first pulse of x-rays and a second pulse of x-rays, wherein the plurality of pulses of x-rays comprise the first pulse of x-rays and the second pulse of x-rays, and wherein the second pulse of x-rays is generated subsequent to the first pulse of x-rays, and
in response to the signal indicating for the source to emit the plurality of pulses of x-rays, emit from the source a third pulse of x-rays and a fourth pulse of x-rays, wherein the source emits the third pulse of x-rays while emitting the fourth pulse of x-rays.

6. The system of claim 5, wherein:
the image acquisition control signal indicates for the source to emit the plurality of pulses of x-rays;
the third pulse of x-rays has a first magnitude for a first period of time;
the fourth pulse of x-rays has a second magnitude for a second period of time; and
the first period of time is different than the second period of time.

7. The system of claim 6, wherein:
the source is configured to emit (i) a fifth pulse of x-rays consecutively after the third pulse of x-rays, and (ii) a sixth pulse of x-rays consecutively after the fourth pulse of x-rays; and
a length of a third period of time between the third pulse of x-rays and the fifth pulse of x-rays is different than a length of a fourth period of time between the fourth pulse of x-rays and the sixth pulse of x-rays.

8. The system of claim 7, wherein a ratio of the first period of time to the third period of time is different than a ratio of the second period of time to the fourth period of time.

9. The system of claim 7, wherein:
the second period of time is longer than the first period of time; and
the image acquisition control module is configured to delay the source from generating the fifth pulse of x-rays and the sixth pulse of x-rays until at least a predetermined period of time after the fourth pulse of x-rays to reduce afterglow of a detector as a result of the detector receiving the third pulse of x-rays and the fourth pulse of x-rays.

10. The system of claim 7, wherein:
the second period of time is longer than the first period of time; and
the source is configured to emit the fifth pulse of x-rays and the sixth pulse of x-rays a predetermined period of time after the fourth pulse of x-rays to reduce afterglow of a detector as a result of the detector receiving the third pulse of x-rays and the fourth pulse of x-rays.

11. The system of claim 5, wherein:
the source is configured to, in response to the control signal indicating for the source to provide the gated output, emit (i) the first pulse of x-rays having a first magnitude for a first period of time, and (ii) the second pulse of x-rays having a second magnitude for a second period of time;
the first magnitude is greater than the second magnitude; and
the first period of time is less than the second period of time.

12. The system of claim 5, wherein:
the source is configured to, in response to the control signal indicating for the source to emit the plurality of pulses of x-rays, emit (i) the third pulse of x-rays having a first magnitude for a first period of time, and (ii) the fourth pulse of x-rays having a second magnitude for a second period of time;
the first magnitude is greater than the second magnitude; and
the first period of time is less than the second period of time.

13. The system of claim 5, wherein:
the source is configured to, in response to the control signal indicating for the source to provide the gated output, emit (i) the first pulse of x-rays having a first magnitude for a first period of time, and (ii) the second pulse of x-rays having a second magnitude for a second period of time;
the first magnitude is greater than the second magnitude;
the first period of time is less than the second period of time;
the source is configured to, in response to the control signal indicating for the source to provide the single pulse of x-rays, emit the single pulse of x-rays having a third magnitude for a third period of time;
the source is configured to, in response to the signal indicating for the source to emit the plurality of pulses of x-rays, emit (i) the third pulse having a fourth magnitude for a fourth period of time, and (ii) the fourth pulse having a fifth magnitude for a fifth period of time;
the fourth magnitude is greater than the fifth magnitude; and
the fourth period of time is less than the fifth period of time.

14. The system of claim 1, further comprising:
a detector configured to detect the single pulse of x-rays and the plurality of pulses of x-rays; and
the image acquisition control module is configured to reconstruct an image based on an output of the detector.

15. A system comprising:
a source; and
an image acquisition control module configured to generate a control signal, wherein the control signal indicates for the source to emit a first pulse of x-rays and a second pulse of x-rays,
wherein the source is configured to, in response to the control signal, emit the first pulse of x-rays while emitting at least a portion of the second pulse of x-rays, and
wherein the first pulse of x-rays has a different pulse width or a different duty cycle than the second pulse of x-rays.

16. The system of claim 15, wherein:
the image acquisition control module is configured to (i) determine whether to emit a single pulse of x-rays from the source or a plurality of pulses of x-rays from the source, and (ii) generate the control signal based on the determination;
the plurality of pulses of x-rays comprise the first pulse of x-rays and the second pulse of x-rays; and
the source is configured to, based on the control signal, emit the single pulse of x-rays or the plurality of pulses of x-rays.

17. The system of claim 15, wherein the first pulse of x-rays has a different pulse width than the second pulse of x-rays.

18. The system of claim 15, wherein the first pulse of x-rays has a different duty cycle than the second pulse of x-rays.

19. A method comprising:
determining whether to emit a single pulse of x-rays or a plurality of pulses of x-rays;
generate a control signal based on the determination;
in response to the control signal indicating emission of the single pulse of x-rays, emit the single pulse of x-rays to have a different magnitude or a different pulse width than one of the plurality of pulses of x-rays; and
in response to the control signal indicating emission of the plurality of pulses of x-rays, (i) emit the one of the plurality of pulses of x-rays to have a different magnitude or a different pulse width than the single pulse of x-rays, or (ii) emit a first pulse of x-rays while emitting at least a portion of a second pulse of x-rays, wherein the first pulse of x-rays has a different pulse width or a different duty cycle than the second pulse of x-rays.

20. The method of claim 19, comprising, in response to the control signal indicating emission of the single pulse of x-rays, emitting the single pulse of x-rays having a different magnitude than one of the plurality of pulses of x-rays.

21. The method of claim 19, comprising, in response to the control signal indicating emission of the single pulse of x-rays, emitting the single pulse of x-rays having a different pulse width than one of the plurality of pulses of x-rays.

22. The method of claim 19, comprising, in response to the control signal indicating emission of the plurality of pulses of x-rays, emitting one of the plurality of pulses of x-rays having a different magnitude or a different pulse width than the single pulse of x-rays.

23. The method of claim 19, comprising, in response to the control signal indicating emission of the plurality of pulses of x-rays, emitting the first pulse of x-rays while emitting at least a portion of the second pulse of x-rays.

24. The method of claim 19, comprising, in response to the control signal indicating emission of the plurality of pulses of x-rays, (i) emitting the one of the plurality of pulses of x-rays having a different magnitude or a different pulse width than the single pulse of x-rays, and (ii) emitting the first pulse of x-rays while emitting at least a portion of the second pulse of x-rays.

* * * * *

UNITED STATES PATENT AND TRADEMARK OFFICE
CERTIFICATE OF CORRECTION

PATENT NO. : 10,292,667 B2
APPLICATION NO. : 14/286717
DATED : May 21, 2019
INVENTOR(S) : Jigney Shah It is certified that error appears in the above-identified patent and that said Letters Patent is hereby corrected as shown below:

In the Specification

Column 7, Line 31:
Delete "122" and insert --120-- therefore;

Column 8, Line 48:
Delete "108." and insert --102.-- therefore;

Column 8, Line 58:
Before "user", delete "input";

Column 8, Line 60:
Delete "22." and insert --24.-- therefore.

Signed and Sealed this
Eleventh Day of February, 2020

Andrei Iancu
*Director of the United States Patent and Trademark Office*